(12) United States Patent
Bolm et al.

(10) Patent No.: US 6,403,522 B1
(45) Date of Patent: Jun. 11, 2002

(54) POLYMERIC HOMOGENEOUS CATALYSTS

(75) Inventors: Carsten Bolm; Joerg Brozio; Christian Dinter; Hartwig Hoecker, all of Aachen; Andreas Seger, Loerrach, all of (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 09/556,189

(22) Filed: Apr. 21, 2000

(30) Foreign Application Priority Data

Apr. 21, 1999 (EP) .......................................... 99 107886

(51) Int. Cl.⁷ .............................................. B01J 31/00
(52) U.S. Cl. ...................... 502/155; 502/152; 502/156; 502/169
(58) Field of Search ................................ 502/152, 155, 502/156, 169

(56) References Cited

U.S. PATENT DOCUMENTS

| | | | |
|---|---|---|---|
| 4,883,851 A | | 11/1989 | Grubbs et al. |
| 5,840,238 A | * | 11/1998 | Setiabundi et al. ......... 526/172 |
| 5,854,299 A | * | 12/1998 | Muhlebach et al. ........ 526/171 |
| 6,008,306 A | * | 12/1999 | Hafner et al. ................ 526/172 |
| 6,162,883 A | * | 12/2000 | Muhlebach et al. ........ 502/152 |

FOREIGN PATENT DOCUMENTS

EP 0901997 A1 3/1999

OTHER PUBLICATIONS

D. Seebach et al, "Polymer–and Dendrimer–Bound Ti–TADDOLates in Catalytic (and Stoichiometric) Enantioselective Reactions: Are Pentacoordinate Cationic Ti Complexes the Catalytically Active Species?" Helvetica Chimica Acta, (1996), vol. 79, pp. 1710–1740.
Bolm et al, "Asymmetrische Dihydroxylierung mit Polyethylenglycolmonomethylether–gebundenen Liganden", Angew. Chem., (1997), vol. 109, No. 7, pp. 773–775.
Minutolo et al, "Polymer–Bound Chiral (Salen)Mn(III) Complex as Heterogeneous Catalyst in Rapid and Clean Enantioselective Epoxidation of Unfunctionalised Olefins", Tetrahedron Letters, (1997), vol. 37, No. 19, pp. 3375–3378.
Beliczey et al., "Novel ligands derived from S–tyrosine for the enantioselective addition of diethylzinc to aldehydes", Tetrahedron: Asymmetry, (1997), vol. 8, No. 10 pp. 1529–1530.

I. Ojima, Catalytic Asymmetric Synthesis, Preface and Appendix Wiley–VCH, 1993.
Shui–Yu Lu et al, "Aqueous ring–opening metathesis polymerisation of 7–oxanorbornene derivatives with oxygen––containing functionalities", Macromolecular Chemistry and Physics, (195(1994) Apr., No. 4, Basel, CH, pp. 1273–1288.

* cited by examiner

*Primary Examiner*—Mark L. Bell
*Assistant Examiner*—J. Pasterczyk
(74) *Attorney, Agent, or Firm*—Oblon, Spivak, McClelland, Maier & Neustadt, P.C.

(57) ABSTRACT

A homogenous catalyst is prepared by reacting a ruthenium or molybdenum carbene catalyst of formula (I):

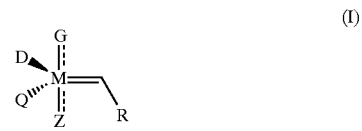

(I)

in a non-reactive organic solvent or solvent mixture with a bicyclic olefin of formula (II):

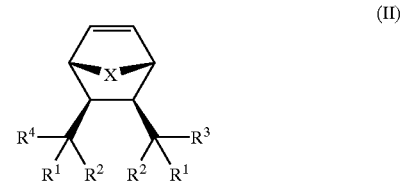

(II)

wherein

X is O, $NR^1$, $C(R^1)_2$, S, $POR^6$, or $PR^6$;

$R^1$ and $R^2$ independently of each other, are H, $(C_1-C_8)$-alkyl, $(C_2-C_8)$-alkenyl, $(C_2-C_8)$-alkynyl, $(C_6-C_{18})$-aryl, $(C_7-C_{19})$-aralkyl, $(C_3-C_{18})$-heteroaryl, $(C_4-C_{19})$-heteroaralkyl, $(C_3-C_8)$-cycloalkyl, $(C_3-C_8)$-cycloalkenyl, $(C_6-C_{18})$-aryl-$(C_1-C_8)$-alkyl, $(C_3-C_{18})$-heteroaryl-$(C_1-C_8)$-alkyl, $(C_3-C_8)$-cycloalkyl-$(C_1-C_8)$-alkyl, or $(C_1-C_8)$-alkyl-$(C_3-C_8)$-cycloalkyl, or form together an =O group;

$R^3$ and $R^4$, independently of each other are $OR^1$, $SR^1$, $NR^1_2$, $OR^7$, $SR^7$, or $NR^1R^7$ provided that at least one residue $R^3$ or $R^4$ bears a group $R^7$, $R^6$ is $R^1$, provided that $R^6$ is not H;

$R^7$ is a catalytically active group, and optionally with a further olefinic compound (III).

12 Claims, No Drawings

POLYMERIC HOMOGENEOUS CATALYSTS

BACKGROUND OF THE INVENTION

1. Field of the Invention

The present invention relates to a polymeric homogeneous catalyst containing an unsaturated polymer backbone. The polymeric backbone is generated by a ring opening metathesis polymerization reaction (ROMP).

2. Description of the Background

Polymeric catalysts are considered to be quite promising for the production of chemical compounds on an industrial scale due to their possible reuse, which, of course, is expected to provide a substantial reduction in production cost.

Recently, emphasis has been placed on the production of homogeneous forms of catalysts, in particular, because the omission of phase transitions during such catalysis leads to an increase in predictability of the reaction behavior of such catalysts. One of the principal reasons for evaluating increasingly sophisticated catalysts lies in the generation of products in enhanced yields and shorter time periods, i.e., in a more economical way.

The desirability of a catalytic system is predicated upon whether the synthesis of the polymeric portion of such catalysts is facile. DE 19910691.6 and DE 19647892.8 offer different solutions for this problem. Nevertheless, a need still exists for the production of new and different polymeric backbones for such compounds with superior properties.

Conventional polymerically—enlarged homogeneous catalysts exhibit more or less randomly distributed catalytically active sites along their polymeric backbone and contain an irregular polymer chain, which can deleteriously affect catalytic behavior.

SUMMARY OF THE INVENTION

It is, therefore, an object of the present invention to provide a polymerically-enlarged homogeneous catalyst exhibiting a polymeric backbone which is more rigid than conventional ones, and which is, nevertheless, easy to synthesize.

It is also an object of the present invention to provide a method of making the polymerically-enlarged homogeneous catalyst.

It is, moreover, yet another object of the present invention to provide a method of using the present polymerically-enlarged homogeneous catalyst.

The above objects and others are provided by a homogeneous catalyst obtained by reacting a compound of the formula (I), as shown hereinbelow in the specification, in a non-reactive organic solvent or solvent mixture with a bicyclic olefin of the formula (II), as shown hereinbelow in the specification.

DETAILED DESCRIPTION OF THE PREFERRED EMBODIMENTS

The prevention invention provides catalysts, methods of using the same and a method of making the catalysts, the latter of which entails reacting a compound of the formula (I)

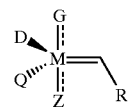

wherein:
D and Q each independently are Cl, Br, I, or OR;
G and Z each independently are $PR'_3$, NR' or D;
R' is $(C_6-C_{18})$-aryl, $(C_3-C_{18})$-heteroaryl, $(C_3-C_8)$-cycloalkyl, $(C_1-C_8)$-alkyl, $(C_6-C_{18})$-aryl-$(C_1-C_8)$-alkyl, $(C_3-C_{18})$-heteroaryl-$(C_1-C_8)$-alkyl, $(C_7-C_{19})$-aralkyl, or $(C_4-C_{19})$-heteroaralkyl;
M is Ru or Mo;
R is $(C_6-C_{18})$-aryl, $(C_3-C_{18})$-heteroaryl, $(C_3-C_8)$-cycloalkyl, $(C_3-C_8)$-cycloalkenyl, H, $(C_1-C_8)$-alkyl, or $(C_2-C_8)$-alkenyl;
in a non-reactive organic solvent or solvent mixture with a bicyclic olefin of the formula (II):

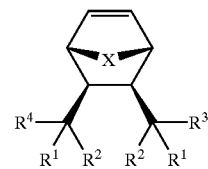

wherein
X is O, $NR^1$, $C(R^1)_2$, S, $POR^6$, or $PR^6$;
$R^1$ and $R^2$ are each independently H, $(C_1-C_8)$-alkyl, $(C_2-C_8)$-alkenyl, $(C_2-C_8)$-alkynyl, $(C_6-C_{18})$-aryl, $(C_7-C_{19})$-aralkyl, $(C_3-C_{18})$-heteroaryl, $(C_4-C_{19})$-heteroaralkyl, $(C_3-C_8)$-cycloalkyl, $(C_3-C_8)$-cycloalkenyl, $(C_6-C_{18})$-aryl, $(C_1-C_8)$-alkyl, $(C_3-C_{18})$-heteroaryl-$(C_1-C_8)$-alkyl, $(C_3-C_8)$-cycloalkyl-$(C_1-C_8)$-alkyl, $(C_1-C_8)$-alkyl-$(C_3-C_8)$-cycloalkyl, or together form an =O group;
$R^3$ and $R^4$, independently of each other, are $OR^1$, $SR^1$, $NR_2^1$, $OR^7$, $SR^7$, or $NR^5R^7$ provided that at least one residue of $R^3$ and $R^4$ bears a group $R^7$;
$R^6$ is $R^1$, with the proviso that $R^6$ is not H; and
$R^7$ is a catalytically active group;
and optionally with a further olefinic compound (III), which is preferably a cycloolefinic compound.

Polymerically enlarged homogeneous catalysts with a rigid unsaturated polymer backbone can be obtained advantageously in a highly modular way, and thus allow a flexible process optimization by combining independently selected bicyclic framework and catalytically active subunits.

In the formula (I), the dashed lines denote the possibility that groups G and Z can be connected to the central atom via a double bond or normal bond. For NR' as a ligand, for example, and Mo as a central atom, this is the case. Nevertheless, in the case of $PR_3'$ as a ligand and Ru as a central atom a normal bond exists in between.

Compounds of the formula (I) and (II) can be mixed in any proportion. Compound (III) can optionally be added to this mixture, preferably in a range from 0–100 times by weight of the sum of I and II, most preferably between 0–10 times by weight.

In accordance with the present invention, the catalytically activwe subunits embrace the subunit itself optionally combined with a linker between active site and polymer backbone. Such linking molecules are known to those skilled in the art, and may be introduced into the molecule in question by processes known in the art according to the demands of space and electronic behavior of the reaction, as shown below.

Linkers, which are feasible, are alkylenic, arylenic or silylenic linkers, for example. In DE 19910691.6 further linkers are disclosed, which are noted hereinbelow.

In general, any linker or spacer structure may be used which is able to couple the preactive center to the polymer. For example, structures, such as the following may be used.

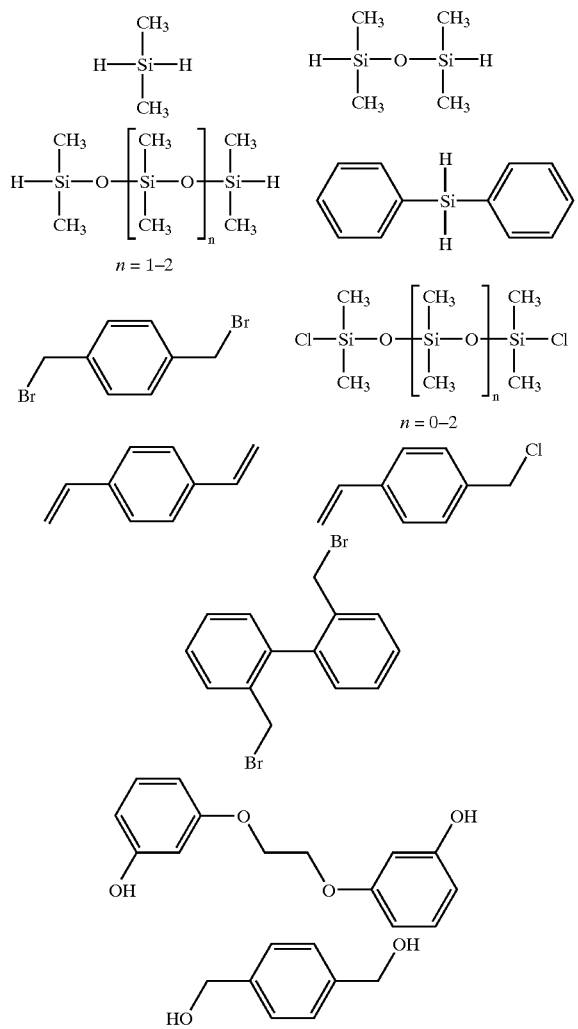

Preferred, however, are spacers such as 1,4'-biphenyl, 1,2-ethylene, 1,3-propylene, PEG-(2–10), α, ω-siloxanylene or 1,4-phenylene as well as α, ω-1,4-bisethylenebenzene. Especially preferred are spacers which can be obtained starting from siloxanes of the formula (II):

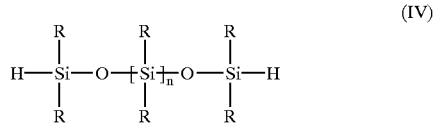

(IV)

These can be easily linked to the double bonds in the polymers and suitable functional groups of the preactive centers under hydrosilylization conditions (the hydrosilyl-ization reaction is reviewed by Ojima in *The Chemistry of Organic Silicon Compounds,* 1989, John Wiley & Sons Ltd., 1480–1526).

Any low molecular weight catalyst familiar to the person skilled in the art of organic synthesis is suitable as the active center in the polymer-enlarged catalysts. A review of this subject is presented by Noyori in *Asymmetric Catalysis in Organic Synthesis,* Wiley-Interscience Publication 1994, Chapter 2, 4, 5, by Ojima in *Catalytic Asymmetric Synthesis,* Wiley-VCH, 1993, and by Bolm and Beller in *Transition Metals for Organic Synthesis,* Vol. II, Chap. 1 and 2, VCH, 1998.

Preferred catalysts, however, are those from the group of catalysts for transfer hydrogenation and hydrogenation with elemental hydrogen, as are catalysts for the aldol reaction and Mukaijama aldol reaction, dialkyl addition to carbonyl groups, Jacobsen epoxidation, Sharpless dihydroxylation, the Diels-Alder and hetero Diels-Alder reaction, enantiose-lective anhydride opening, the reduction of ketones with hydrides and the Heck reaction.

The further olefinic compound (III) may be any organic molecule, which contains at least one double bond and which is known to those skilled in the art to be suitable for reacting in a ring opening metathesis reaction. This olefinic compound serves as a means for copolymerization and dilutes the number of active sites per unit of length within the polymeric backbone. Therefore, this is another manner of adapting the catalysts of the present invention to the most suitable demands of space necessary for the reaction in question.

Preferred compounds are ethylene, propene, butene, pentene, isobutene, isopropene and cyclic olefines like cyclopropene, cyclobutene, cyclopentene, cyclopentadiene, cyclohexene, and cycloheptene, for example. Bicyclic olefinic compounds, such as norbornene or azulene, for example, may also be used.

Preferred are catalysts wherein R is Ph, X is O, $R^1$, $R^2$ form together an =O group, $R^3$ is $R^4$, $O(C_1$–$C_3)$-alkyl, and where $R^4$ is $OR^7$, $R^7$ is a catalytically active group of alcohols, amines, phosphines, or other sulfur or phosphorus-containing groups.

More preferably, the catalysts of the present invention have a residue $R^7$, which is a compound of the catalysts mentioned in DE 19910691.6, as suitable for various chemical reactions.

Most preferred are catalysts, such as, for example, Taddol-ligands (Seebach, *Helv. Chim. Acta,* 1996, 79, 1710f.), chiral salene-complexes (Salvadori), *Tetrahedron Lett.,* 37, 1996, 3375f.), ligands for Sharpless-dihydroxylation like dihydrochinidines (Bolm, i Angew. Chem., 1997, 773f.), 1,2-diaminealcohols (Wandrey, *Tetrahedron: Asymmetry,* 1997, 8, 1529f.) or hydrogenation catalysts like 1,2-diphosphane-ligands, for example DIOP, DIPAMP; BPPFA, BPPM, CHIRAPHOS, PROPHOS, NORPHOS, BINAP, CYCPHOS, SKEWPHOS 5 (BDPP), DEGPHOS, DUPHOS und PNNP.

Most preferred are the catalysts described in EP 305180, particularly 2-(hydroxydiphenylmethyl)pyrrolidin-4-yl as the active center.

As already mentioned, the catalysts of the present invention can be produced by procedures well known to those skilled in the art with or without linkers between the active subunit and the backbone.

Advantageously, a compound of the formula (1):

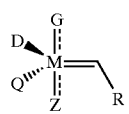
(I)

wherein:
D and B each independently are Cl, Br, I, or OR;
G and Z each independently are PR'$_3$, NR' or D;
R' is (C$_6$–C$_{18}$)-aryl, (C$_3$–C$_{18}$)-heteroaryl, (C$_3$–C$_8$)-cycloalkyl, (C$_1$–C$_8$)-alkyl, (C$_6$–C$_{18}$)-aryl-(C$_1$–C$_8$)-alkyl, (C$_3$–C$_{18}$)-heteroaryl-(C$_1$–C$_8$)-alkyl, (C$_7$–C$_{19}$)-aralkyl, or (C$_4$–C$_{19}$)-heteroaralkyl;
M is Ru or Mo;
R is (C$_6$–C$_{18}$)-aryl, (C$_3$–C$_{18}$)-heteroaryl, (C$_3$–C$_8$)-cycloalkyl, (C$_3$–C$_8$)-cycloalkenyl, H, (C$_1$–C$_8$)-alkyl, or (C$_2$–C$_8$)-alkenyl;
is reacted in a non-reactive organic solvent or solvent mixture with a bicyclic olefin of the formula (II):

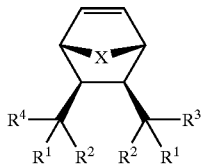
(II)

wherein:
X is O, NR$^1$, C(R$^1$)$_2$, S, POR$^6$, or PR$^6$;
R$^1$ and R$^2$, independently of each other, are H, (C$_1$–C$_8$)-alkyl, (C$_2$–C$_8$)-alkenyl, (C$_2$–C$_8$)-alkynyl, (C$_6$–C$_{18}$)-aryl, (C$_7$–C$_{19}$)-aralkyl, (C$_3$–C$_{18}$)-heteroaryl, (C$_4$–C$_{19}$)-heteroaralkyl, (C$_3$–C$_8$)-cycloalkyl, (C$_3$–C$_8$)-cycloalkenyl, (C$_6$–C$_{18}$)-aryl, (C$_1$–C$_8$)-alkyl, (C$_3$–C$_{18}$)-heteroaryl-(C$_1$–C$_8$)-alkyl, (C$_3$–C$_8$)-cycloalkyl, (C$_1$–C$_8$)-alkyl, or (C$_1$–C$_8$)-alkyl-(C$_3$–C$_8$)-cycloalkyl, or form together an =O group;
R$^3$ and R$^4$, independently of each other, are OR$^1$, SR$^1$, NR$^1_2$, OR$^7$, SR$^7$, NR$^1$R$^7$, provided that at least one residue of R$^3$ and R$^4$ bears a group R$^7$;
R$^6$ is R$^1$, provided that R$^6$ is not H; and
R$^7$ is a catalytically active group, and optionally with a further olefinic compound (III), preferably a cycloolefinic compound. wherein:

Preferably a process is chosen, in which compounds (I) and (II) are used wherein R is Ph, X is O, R$^1$, R$^2$ form together an =O group, R$^3$ is R$^4$, O(C$_1$–C$_8$)-alkyl, and R$^4$ is OR$^7$, where R$^7$ is a catalytically active group.

Most preferred is a process, where R$^7$ is a compound selected from above preferred active groups.

A feasible non-reactive organic solvent or at least part of the solvent mixture is a haloalkane, such as, for example, dichloromethane. The process is preferably conducted at temperatures between about −20° C. to 50° C., more preferably between about −5° C. and 30° C. and most preferably between 5° C. and 25° C.

The catalysts according to the present invention can be used for organic synthesis. It is preferred that they are used in a reactor, which is able to retain the polymerically enlarged homogeneous catalysts, while permitting the starting material to be introduced in and the product to be released from the reactor. More preferably these catalysts are used in a membrane reactor. Such reactions and reaction conditions are specified in DE 19910691.6, and are incorporated by reference herein in the entirety. When using optically enriched catalysts according to the present invention, a use in a process for the production of optically active compounds is most preferred.

The following scheme illustrates one manner of synthesizing the catalysts of the present invention.

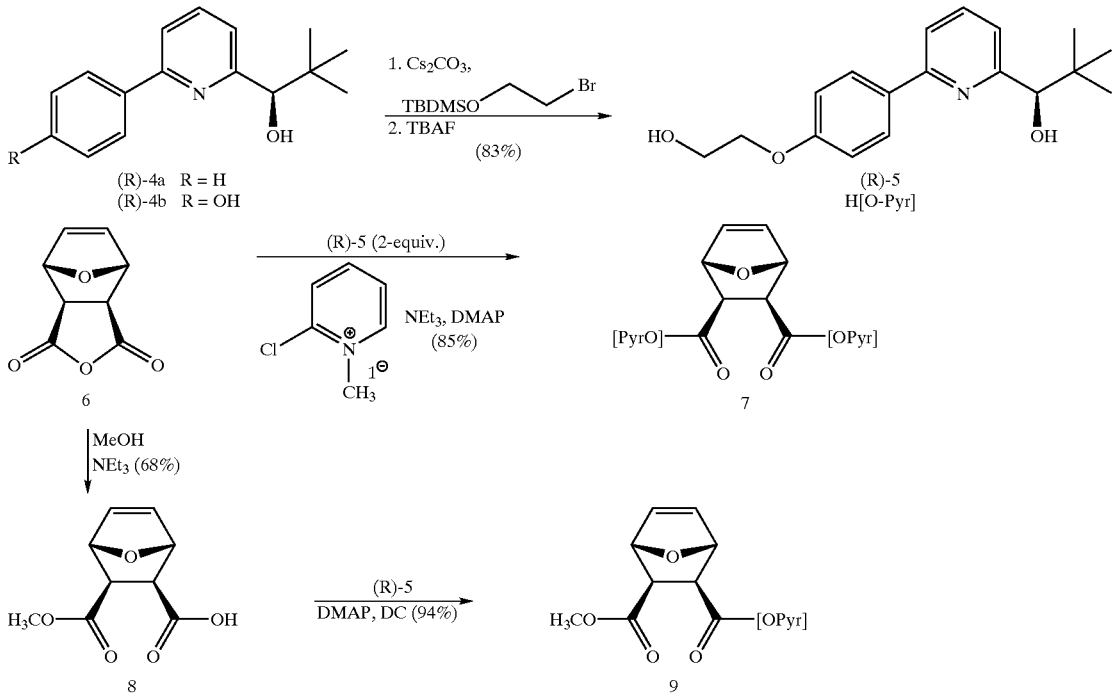

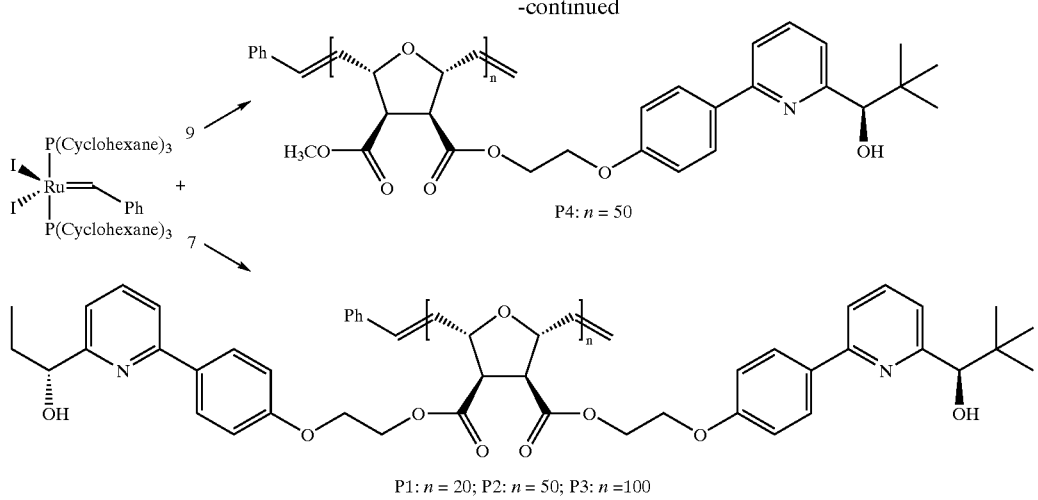

P4: n = 50

P1: n = 20; P2: n = 50; P3: n =100

The catalyst made are employed in a diethyl zinc addition to benzaldehyde as a probe reaction. The results are shown below in Table 1.
Table 1: Reaction of Benzaldehyde and Diethyl Zinc Catalyzed by Various Pyridinyl Alcohols

TABLE 1

Reaction of benzaldehyde and diethyl zinc catalyzed by various pyridinyl alcohols $$PhCHO + ZnEt_2 \xrightarrow[\text{2. work-up}]{\text{1. catalyst}} PhC * H(OH)Et$$

10                                  11

| Pyridinyl alcohol/polymer | $\overline{M}_w/\overline{M}_n$ | Time [h] | Yield of 11 [%] | Ee of 11 [%][a] |
|---|---|---|---|---|
| 4a | — | 4[b] | 91 | 87 |
| 5 | — | 24[c] | 86 | 83 |
| 7 | — | 24[b] | 72 | 79 |
| 9 | — | 24[c] | 89 | 80 |
| P1 | 1.2 | 48[b] | 88 | 73 |
| P2 | 1.4 | 48[b] | 83 | 73 |
| P3 | 1.7 | 48[b] | 77 | 73 |
| P4 | 1.1 | 48[c] | 78 | 71 |

[a]Determined by HPLC using a chiral stationary phase.
[b]Reaction was performed at 0° C.
[c]Reaction was performed at room temperature.

It is clear from these experiments that the catalysts of the present invention function as versatile tools in homogeneous catalytic organic reactions.

It is explicitly contemplated that each single structure of the chiral catalysts of the present invention includes all and every possible diastereomer whether in racemic form or optically enriched. Each of such diastereomers explicitly embraces and discloses the possible enantiomers as well.

Also explicitly contemplated are the linear or branched ($C_1$–$C_8$)-alkyl radicals methyl, ethyl, n-propyl, isopropyl, n-butyl, isobutyl, sec-butyl, tert-butyl, pentyl, hexyl, heptyl or octyl, as well as all constitutional isomers. The linear or branched ($C_2$–$C_8$)-alkenyl radicals include all substituents listed above in connection with the ($C_1$–$C_8$)-alkyl radical with the exception of the methyl radical, there being at least one double bond present in those radicals. The scope of ($C_2$–$C_8$)-alkynyl corresponds to that of ($C_2$–$C_8$)-alkenyl, but at least one triple bond must be present in that case. ($C_3$–$C_8$)-cycloalkyl is to be understood as being cyclopropyl, cyclobutyl, cyclopentyl, cyclohexyl, cycloheptyl or cyclooctyl radicals.

($C_3$–$C_8$)-cycloalkenyl denotes cycloalkylic radicals containing one or more double bonds within the residue. ($C_6$–$C_{18}$)-aryl denotes arylic species with 6 to 18 carbon atoms, like phenyl, naphthyl, phenanthryl. ($C_7$–$C_{19}$)-aralkyl are arylic radicals connected via a ($C_1$–$C_8$)-alkyl radical with the molecule of respect, for example benzyl, 1-, 2-phenylethyl, naphthylmethyl. ($C_3$–$C_{18}$)-heteroaryl are arylic molecules in which at least one C-atom is substituted by a heteroatom such as N, O, P, S. Molecules, which may be mentioned, for example, are pyrolyl, furyl, pyridyl, and imidazolyl. ($C_4$–$C_{19}$)-heteroaralkyl are heteroarylic species bonded via a ($C_1$–$C_8$)-alkyl radical with the molecule in question, such as furfuryl, pyrolylmethyl, pyridylmethyl, furyl-1-, 2-ethyl or pyrolyl-1-, 2-ethyl.

EXPERIMENTAL SECTION n-Butyl lithium was purchased from Merck-Schuchardt as a 1.6 M solution in n-hexane, diethylzinc was provided as a gift from Witco. Bis(tricyclohexylphosphine)benzylidenruthenium(II) dichloride was purchased from Strem, (−)-B-chlorodiisopinocampheylborane 'DIP Chloride™ from Aldrich. Tetrakis(triphenylphosphine)palladium (O) was donated by Degussa. THF, diethylether, and toluene were distilled from sodium/benzophenone ketyl radical under argon. Dichloromethane was distilled from $CaH_2$ under argon. All other solvents were reagent grade ant used as received.

Unless otherwise stated, as used herein, the term "standard work-up" refers to quenching a reaction mixture with water, followed by extraction with organic solvent. Subsequently, washing of the organic layer is effected with brine and water, and the combined organic phases are dried with anhydrous $MgSO_4$. Finally, solvent is evaporated under reduced pressure the afford the crude product.

All syntheses of the monomeric and polymeric catalysts and all catalyses were repeated at least twice in order to ensure reproducibility. Thus, stated yields are average values. The enantiomeric excess of phenylpropanol was determined by means of HPLC using a chiral column (Chiralcel OD).

1. Syntheses of the Monomeric Precursors exo-7-(Oxabicyclo [2.2.1]hept-5-ene-2,3-dicarboxylic acid anhydride (6)

A dry Schlenk flask under argon was filled with maleic anhydride (9.81 g, 100 mmol) and 50 mL toluene. The mixture was warmed to 80° C., and then furan (10.21 g, 150 mmol) was added. After stirring for 24 hours at room temperature the mixture was cooled to 0° C., and the solid product was filtered off and washed with 30 mL methyl tert-butylether. Drying in vacuo furnished 11.78 g (71%) of (6) as a fine white powder. Mp: 116° C. (decomposition).$^1$H NMR (300 MHZ, CDCl$_3$): δ3.16 (s, 2H); 5.43 (s, 2H); 6.55 (s, 2H). $^{13}$C NMR (75 MHZ, CDCl$_3$): δ48.7; 82.1; 136.9; 169.9 Reference: Furdik, M.; Drabek, J. *Tetrahedron* 1973, 29, 2445.

rac-7-Oxabicyclo[2.2.1]hept-5-ene-2,3-dicarboxylic acid monomethylester (8)

Triethylamine (0.51 g, 5 mmol) was added dropwise to a suspension of exo-7-oxabicyclo[2.2.1]hept-5-ene-2,3-dicarboxylic acid anhydride (6) (4.15 g, 25 mmol) in 25 mL of methanol and the mixture was stirred for 24 hours at room temperature. After removal of methanol, the residue was dissolved in 25 mL of dichloromethane, and the resulting solution was washed subsequently with 7 mL of 1 M hydrochloric acid and 10 mL brine, followed by drying the organic phase with anhydrous MgSO$_4$. Evaporation of the solvent under reduced pressure yielded 3.37 g (68%) of (8) as a pale yellow solid. Mp: 110° C. $^1$H NMR (300 MHZ, CDCl$_3$): δ2.86 (s, 2H); 3.71 (s, 3H); 5.27 (s, 1H); 5.31 (s, 1H); 6.48 (s, 2H); 10.20 (s, 1H) $^{13}$C NMR (75 MHZ, CDCl$_3$): δ46.9: 47.2; 52.3; 80.4;80.6; 136.4; 136.8; 171.8; 177.3. Reference: Guanti, G.; Narisano, E; Riva, R.; Thea, S. *Tetrahedron Lett.* 1986, 38, 4639.

Synthesis of (R)-1-{6-[4-(2-hydroxyethoxy)phenyl]pyridin-2-yl}-2,2-dimethylpropanol (5)

a) 4-(tert-Butyl dimethylsiloxy)phenylboronic acid

Magnesium turnings (0.53 g, 22 mmol) and 20 mL of THF were placed into a two-necked flask. Next, tert-butyldimethylsilyloxyphenyl bromide (5.64 g, 19.6 mmol) was added and the mixture was heated under reflux for 2 h before it was cooled to room temperature. The brown mixture was added to a solution of trimethyl borate (2.43 g, 24 mmol) in 5 mL of THF through a dropping funnel at −78° C. and allowed to warm to room temperature overnight. After hydrolysis with 90 mL of ca. 0.1 M hydrochloric acid followed by standard work-up with methyl tert-butyl ether, the brown residue was washed with 20 mL of cold hexane, and the resulting white product (3.86 g, 78%) was dried in vacuo. Mp: 175° C. ($^1$H NMR (300 MHZ, CDCl$_3$): δ0.25 (s, 6H); 1.01 (s, 9H); 6.95 (d, J=8.5 Hz, 2H); 8.11 (d, J 8.5 Hz, 2H). $^{13}$C NMR (75 MHZ, CDCl$_3$): δ−4.3; 18.1; 25.7; 119.8; 137.5; 159.8. Reference: Bolm, C.; Derrien, N.; Seger, A. *Synlett* 1996, 387.

b) (R)-1-[6-(4-Hydroxyphenyl)-pyridin-2-yl]-2,2-dimethylpropanol (4b)

Tetraki~(triphenylphosphine)palladium(O) (1.16 g, 1 mmol) were dissolved in 50 mL of toluene in a two-necked flask under argon. Then, (R)-1-(6-bromopyridin-2-yl)-2,2-dimethylpropanol (4.88 g, 20 mmol) was added to the yellow suspension. Subsequently, solutions of sodium carbonate (4.24 g, 40 mmol) in 20 mL of distilled water and 4-(tert-butyldimethylsiloxy)phenylboronic acid in 25 mL of methanol were added and the mixture was heated under reflux for 6.5 hours. After cooling to room temperature the reaction was quenched with 120 mL of saturated sodium carbonate solution and 20 mL of aqueous ammonia. The aqueous layer was extracted five times with dichloromethane, and the combined organic phases were washed with brine. Drying with anhydrous MgSO$_4$ and evaporation of the solvents under reduced pressure gave the crude product which was dissolved in 50 mL of THF. Next, 22 mL of TBAF (1 M in THF) were added and the mixture was stirred for 5 hours at room temperature. Standard work-up with dichloromethane gave crude (4b) which was purified by column chromatography followed by recrystallization from toluene/hexane (2:1) to give 4.35 g (85%) of (4b) as white needles. The enantiomeric excess was determined by means of HPLC using a chiral column [Chiracel OD; eluent: n-heptane/iso-propanol=85:15; flow: 1.0 mL/min; t$_R$=8.2 min; (R); 10.3 min (S)] Mp: 130° C. [α]$_D$=−18.4 (c=2.32, acetone). $^1$H NMR (300 MHZ, CDCl$_3$): δ0.98 (s, 9H); 4.46 (s, 1H); 5.50 (s, 1H); 6.96 (d, J=8.8 Hz, 2H); 7.06 (dd, J=7.8 Hz, 0.8 Hz, 1H); 7.57 (dd, J=8.0 Hz, 0.8 Hz, 1H); 7.67 (dd, J=7.7 Hz, 1H); 7.89 (d, J=8.8 Hz, 2H). $^{13}$C NMR(75 MHZ, CDCl$_3$): δ=26.0; 36.3; 80.0; 115.8; 118.4; 120.5; 128.3; 130.9; 136.6; 155.1; 157.6; 158.4. MS (70 eV): m/z (%) 257 (M, 4), 200 (100). IR (KBr): 1613, 1571, 1519, 1455, 1282, 1173, 1052, 807 cm$^{-1}$. Anal. Calcd. for C$_{16}$H$_{19}$NO$_2$; C, 74.68; H, 7.44; N, 5.44. Found: C, 74.59; H, 7.37; N, 5.34.

c) (R)-1-{6-[4-(2-Hydroxyethoxy)phenyl]pyridin-2-yl}-2,2-dimethylpropanol (5)

A dry 250 mL three-necked flask was charged with (R)-1-[6-(4-hydroxyphenyl)pyridin-2-yl]-2,2-dimethylpropanol (4b) (2.54 g, 9.9 mmol), cesium carbonate (6.43 g, 19.8 mmol) and 100 mL of acetonitrile. Next, 2-bromoethyl-tert-butyldimethylsilyl ether was added through a dropping funnel. The mixture was heated under reflux for 2 hours and stirred for additional 14 hours at room temperature. After standard work-up with ethyl acetate the crude product was dissolved in 25 mL of THF and 11 mL of TBAF (1 M in THF) were added. After stirring for 1 hour at room temperature, the solution was quenched with 50 mL of water and standard work-up with dichloromethane followed by column chromatography (SiO$_2$, eluent: ethyl acetate/hexanes=1:1) yielded 2.46 g (83%) of (5) as a white powder. Mp: 104° C. [a]$_D$,=−14.4 ©=2.28, acetone). $^1$H NMR (300 MHZ, CDCl$_3$): δ0.96 (s, 9H); 2.36–2.40 (m, 1H); 3.95–4.01 (m, 2H); 4.11–4.15 (m, 2H); 4.39 (d, J=7.4 Hz, 1H); 4.66 (d, J=7.4 Hz, 1H); 7.01 (d, J=8.8 Hz, 2H); 7.06 (dd, J=7.97 Hz, 0.8 Hz, 1H); 7.57 (dd, J=7.97 Hz, 0.8 Hz, 1H); 7.66 (m, 1H); 7.95 (d, J=8.8 Hz, 2H). $^{13}$C NMR (75 MHZ, CDCl$_3$): δ26.0; 36.3; 61.4; 69.4; 80.2; 114.7; 118.2; 120.7; 128.2; 131.9; 136.4; 155.0; 159.3; 159.7. M S 70 eV):m/z(%)301(M, 7),244 (100).IR(KBr): 1608, 1576, 1516, 1453, 1255, 1174, 1046, 812 cm$^{-1}$. Anal. Calcd. for C$_{18}$H$_{23}$NO$_3$: C, 71.73; H, 7.69; N, 4.65. Found: C, 71.59; H, 7.68; N, 4.56.

(R,R )-7-Oxabicyclo[2.2.1]hept-5-ene-(2-exo,3-exo)-dicarboxylic acid b is -(2-{4 [6-(1-hydroxy-2,2-dimethylpropyl)-pyridin-2-yl]phenoxy}ethyl)ester (7)

A dry 25 mL Schlenk flask was charged with exo-7-oxabicylo[2.2.1]hept-5-ene-(2-exo,3-exo)-dicarboxylic acid anhydride (6) (415 ma, 2.5 mmol), (R)-1-(6-[4-(2-hydroxyethoxy)phenyl]pyridin-2-yl)-2,2-dimethylpropanol (5) (1.50 g, 5 mmol) and 15 ml of dichloromethane. Next, triethylamine (759 mg, 7.5 mmol), 4-DMAP (122 ma, 1 mmol) and 2-chloro-1-methylpyridinium iodide (766 mg, 3 mmol) were added, and the resulting yellow mixture was stirred for 48 hours at room temperature. Standard work-up with dichloromethane followed by column chromatography (SiO2, eluent: methyl tert-butyl ether) of the crude product yielded 1.59 g (85%) of (7) as a white solid, which was stored at 0° C. Mp: 70–75° C. [α]$_D$=−12.3 ©=2.10, toluene). $^1$H NMR (300 MHZ, CDCl$_3$): δ0.95 (s, 18H); 2.89 (s, 2H); 4.15–4.22 (m, 4H); 4.36–4.40 (m, 2H); 4.44–4.48 (m, 4H); 4.59–4.65 (m, 2H); 5.28 (s, 2H); 6.45 (s, 2H); 6.95–7.00 (m, 4H); 7.04–7.08 (m, 2H); 7.52–7.56 (m, 2H); 7.61–7.67 (m, 2H); 7.90–7.97 (m, 4H). $^{13}$C NMR (75 MHZ, CDCl$_3$): δ26.0; 36.3; 46.8; 63,5; 65.9; 80.1; 80.8; 114.8; 118.2; 120.7;

128.1; 132.0; 136.3; 136.7; 154.8; 159.3; 159.4; 171.4. MS (70 eV): m/z (%) 625 (M—$C_4H_4O$—$C_4H_9$, 18), 244 (100) IR (KBr): 1747, 1608, 1571, 1515, 1453, 1249, 1180, 1055, 813 $cm^{-1}$. Anal. Calcd for $C_{44}H_{50}N_2O_9$: C, 70.38; H, 6 71; N, 3 73 Found: C, 70.10; H, 6.72; N, 3.51.

7-Oxabicyclo[2.2.1]hept-5-ene-(2-exo,3-exo)-dicarboxylic acid methyl (R)-(2-{4-[6-(1-hydroxy-2,2-dimethyl-propyl)-pyridin-2-yl]phenoxy}ethyl)ester (9)

A dry 100 mL Schlenk flask was filled with 7-oxabicyclo [2.2.1]hept-5-ene-(2-exo,3-exo)-dicarboxylic acid monomethyl ester (8) (595 ma, 3 mmol), (R)-1-{6-[4-(2-hydroxyethoxy)phenyl]pyridin-2-yl}-2,2-dimethylpropanol (995 ma, 3.3 mmol) and 20 mL of dichloromethane. Next, 4-DMAP (55 mg, 0.45 mmol) and DCC (743 g, 3.6 mmol) were added and the mixture was stirred over a period of 24 hours at room temperature. Standard work-up with dichloromethane followed by column chromatography ($SiO_2$, eluent: ethyl acetate/hexane=2:1) afforded (9) as a white solid (1.35 g, 94%). Mp: 54–60° C. $[\alpha]_D$=−7.2 ©=2.08, toluene). $^1H$ NMR (300 MHZ, $CDCl_3$): δ0.96 (s, 9H); 2.86 (s, 2H); 3.69 (s, 3H); 4.22–4.27 (m, 2H); 4.36–4.40 (m, 1H); 4.47–4.52 (m, 2H); 4.61–4.66 (m, 1H); 5.26–5.28 (m, 2H); 6.45 (s, 2H); 6.99–7.03 (m, 2H); 7.05–7.09 (m, 1H); 7.56–7.60 (m, 1H); 7.64–7.69 (m, 1H); 7.94–7.98 (m, 2H). $^{13}C$ NMR (75 MHZ, $CDCl_3$): δ26.0; 36.3: 46.7; 47.0; 52.3; 63.4; 65.9; 80.1; 80.5; 80.6; 114.8; 118.2; 120.7; 128.2; 132.0; 136.4; 136.6; 136.7; 154.8; 159.3; 159.4; 171.5; 171.9. MS (70 eV): m/z (%) 481 (M, 2), 356 (100). IR (KBr): 1747, 1609, 1571, 1516, 1435, 1248, 1180, 1054, 813$^{cm-1}$. Anal. Calcd. for $C_{27}H_{31}NO_7$: C, 67.20; H; 6.49; N, 2.91. Found: C, 67.35; H, 6.82; N, 3.12.

II. Polymerization of Bicyclic Olefins (7) and (9)

A dry Schlenk flask under argon was charged with $RuCl_2$ $(CHC_6H_5)[P(C_6H_{11})3]_2$ (1) which was dissolved in 3 mL of dichloromethane, and a solution of the bicyclic olefin (20, 50 or 100 equiv. of (7); 50 equiv. of 9) in 7 mL of dichloromethane was added. Stirring the mixture for 24 hours at room temperature was followed by the addition of 0.3 mL of ethyl vinylether. After having it stirred for an additional hour, the solution was filtered (silica gel, dichloromethane) to remove the ruthenium catalyst and the solvent was evaporated. The gray/green solids were analyzed by $^1H$ NMR spectroscopy and subjected to GPC.

NMR-spectrospcopy: After the reaction no double bond signals for the bicyclic monomers (δ6.45 ppm) were detected. Instead, broad signals at 5.5 and 5.8 ppm for the olefinic protons in the polymer were observed. For P1, P2, and P3: $^1H$ NMR (300 MHZ, $CDCl_3$): δ0.90 (s); 2.98–3.20 (m); 4.05 (s); 4.36 (s); 4.50–4.72 (m); 5.17 (s); 5.52 (s); 5.84 (s); 6.80–7.04 (m); 7.38–7.62 (m); 7.76–7.92 (m); all signals were broad. For P4: $^1H$ NMR (300 MHZ, $CDCl_3$): δ0.93 (s); 3.10 (s); 3.59 (s); 4.15 (s); 4.32–4.50 (m); 4.55–4.78 (m); 5.10 (s); 5.58 (s); 5.90 (s); 6.88–7.10 (m); 7.44–7.70 (m); 7.86–800 (m); all signals were broad.

GPC analysis: Waters HPLC-pump type 510, flow: 1.0 mL/min, eluent: THE p.a., teflon-membrane filter 0.2 μm, 2 columns, each with a length of 500 mm and a diameter with Jordi DVB-gel of 1000 Å and 100000 Å, respectively; Melz RI-detector LCD 201, calibration: PSS-Polystyrolstandards 500–750.000.

TABLE 2

Polymer yields and characterization

| Polymer | Monomer | Monomer equivalents | Amount of catalyst 1 (mg/μmol) | Polymer yield [%] | $\overline{M}_n$ | $\overline{M}_w$ | $\overline{M}_n/\overline{M}_w$ |
|---|---|---|---|---|---|---|---|
| P1 | 7 | 20 | 24.8/30 | 49[a] | 15500 | 19100 | 1.2 |
| P2 | 7 | 50 | 9.4/11.4 | 98 | 27700 | 38100 | 1.4 |
| P3 | 7 | 100 | 5.0/6.0 | 35[a] | 32200 | 53100 | 1.7 |
| P4 | 9 | 50 | 8.4/10.2 | 99 | 29800 | 33300 | 1.1 |

[a] After additional chromatography through a sephadex column.

III. Diethyl Zinc Addition to Benzaldehyde (10)

A dry Schlenk flask under argon was charged with 0.05 equiv. of the pyridinyl alcohol. The flask was evacuated twice and flushed with argon. Then, 5 mL of freshly distilled toluene were added followed by 1.5 equiv. of neat diethylzinc while stirred. After stirring for 20 min at room temperature, 1.0 equiv. of benzaldehyde (10) was added at the given temperature (see Table). The proceeding of the reaction was monitored by thin layer chromatograpy. After full conversion of the aldehyde, the reaction was quenched by careful addition of 10 mL of 2 M HCl, and the resulting mixture was extracted three times with 25 mL of dichloromethane. The combined organic phases were washed with brine, dried over $MgSO_4$, and the solvent was removed under reduced pressure. The crude product was purified by column chromatography (silica gel, hexane/methyl tert-butylether=10:1) followed by Kugelrohr distillation to give 1-phenylpropanol (11) as a colorless oil. The enantiomeric excess of 11 was determined by HPLC on a stationary phase [CHIRALCEL OD, n-heptane/iso-propanol=98:2, 1 0 mL/min; $t_R$=17.2 min (R); 21.5 min (S)], and the absolute configuration was determined by correlation of the optical rotation with the values reported in the literature (Soai, K.; Ookawa.; Kaba, T.; Ogawa, K.; J. Arn. Chem. Soc. 1987, 109, 7111).

TABLE 3

Reaction of benzaldehyde (10) and diethylzinc catalyzed by various pyridinyl alcohols

| Pyridinyl alcohol/polymer | Amount of pyridinyl alcohol (mg/μmol[a]) | Time [h] | Yield of 11 [%] | Ee of 11 [%] |
|---|---|---|---|---|
| 4a | 15.0/62.1 | 4[b] | 91 | 87 |
| 5 | 15.0/49.8 | 24[c] | 86 | 83 |
| 7 | 16.8/44.6 | 24[b] | 72 | 79 |
| 9 | 38.1/79.1 | 24[c] | 89 | 80 |
| P1 | 22.6/60.2 | 48[b] | 88 | 73 |
| P2 | 23.1/61.5 | 48[b] | 83 | 73 |
| P3 | 48.7/130.0 | 48[b] | 77 | 73 |
| P4 | 35.3/73.0 | 48[c] | 78 | 71 |

Having now fully described the present invention, it will be apparent to one of ordinary skill in the art that many changes and modifications can be made to the embodiments described above without departing from the spirit or scope of the present invention.

What is claimed is:

1. A homogeneous catalyst prepared by reacting a compound of the formula (I):

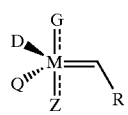

(I)

wherein
- D and Q each independently are Cl, Br, I, or OR;
- G and Z is each independently PR'$_3$, NR' or D;
- R' is $(C_6-C_{18})$-aryl, $(C_3-C_{18})$-heteroaryl, $(C_3-C_8)$-cycloalkyl, $(C_1-C_8)$-alkyl, $(C_6-C_{16})$-aryl-$(C_1-C_8)$-alkyl, $(C_3-C_{18})$-heteroaryl-$(C_1-C_8)$-alkyl, $(C_7-C_{19})$-aralkyl, or $(C_4-C_{19})$-heteroaralkyl;
- M is Ru or Mo;
- R is $(C_6-C_{18})$-aryl, $(C_3-C_{18})$-heteroaryl, $(C_3-C_8)$-cycloalkyl, $(C_3-C_8)$-cycloalkenyl, H, $(C_1-C_8)$-alkyl, or $(C_2-C_8)$-alkenyl;

in a non-reactive organic solvent or solvent mixture with a bicyclic olefin of the formula (II):

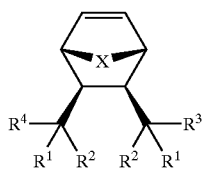

(II)

wherein
- X is O, NR$^1$, C(R$^1$)$_2$, S, POR$^6$, or PR$^6$;
- R$^1$ and R$^2$, independently of each other, are H, $(C_1-C_8)$-alkyl, $(C_2-C_8)$-alkenyl, $(C_2-C_8)$-alkynyl, $(C_6-C_{18})$-aryl, $(C_7-C_{19})$-aralkyl, $(C_3-C_{18})$-heteroaryl, $(C_4-C_{19})$-heteroaralkyl, $(C_3-C_8)$-cycloalkyl, $(C_3-C_8)$-cycloalkenyl, $(C_6-C_{18})$-aryl-$(C_1-C_8)$-alkyl, $(C_3-C_{18})$-heteroaryl-$(C_1-C_8)$-alkyl, $(C_3-C_8)$-cycloalkyl-$(C_1-C_8)$-alkyl, or $(C_1-C_8)$-alkyl-$(C_3-C_8)$-cycloalkyl, or form together an =O group;
- R$^3$ and R$^4$ are independently of each other OR$^1$, SR$^1$, NR$^1_2$, OR$^7$, SR$^7$, or NR$^1$R$^7$ provided that at least one residue R$^3$ or R$^4$ bears a group R$^7$,
- R$^6$ is R$^1$, provided that R$^6$ is not H;
- R$^7$ is a catalytically active group, and optionally with a further olefinic compound (III).

2. The catalyst of claim 1, wherein
- R is Ph;
- R' is Ph, or $(C_1-C_8)$-alkyl;
- X is O;
- R$^1$ and R$^2$ form together an =O group;
- R$^3$ is R$^4$, or O$(C_1-C_8)$-alkyl; or
- R$^4$ is OR$^7$.

3. The catalyst of claim 1, wherein
R$^7$ is a compound comprising Taddol-ligands, chiral salene-complexes, ligands for Sharpless-dihydroxylation, 1,2-diaminoalcoholic groups or hydrogenation catalyst groups having 1,2

4. The catalyst of claim 3, wherein said 1,2-diphosphane-ligands are selected from the group consisting of DIOP, DIPAMP, BPPFA, BPPM, CHIRAPHOS, PROPHOS, NORPHOS, BINAP, CYCPHOS, SKEWPHOS (BDPP), DEGPHOS, DuPHOS and PNNP.

5. The catalyst of claim 1, wherein said further olefinic compound (III) comprises ethylene, propene, butene, pecitene, isobutene, isoprene, cyclopropene, cyclobutene, cyclopentene, cyclopentadiene, cyclohexene, cycloheptene, norbornene, or azulene.

6. A method for producing the homogeneous catalyst of claim 1, which comprises reacting a compound of the formula (I):

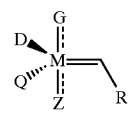

(I)

wherein:
- D and Q each independently are Cl, Br, I, or OR;
- G and Z each independently are PR'$_3$, NR' or D;
- R' is $(C_6-C_{18})$-aryl, $(C_3-C_{18})$-heteroaryl, $(C_3-C_8)$-cycloalkyl, $(C_1-C_8)$-alkyl, $(C_6-C_{18})$-aryl-$(C_1-C_8)$-alkyl, $(C_3-C_{18})$-heteroaryl-$(C_1-C_8)$-alkyl, $(C_7-C_{19})$-aralkyl, or $(C_7-C_{19})$-heteroaralkyl;
- M is Ru or Mo;
- R is $(C_6-C_{18})$-aryl, $(C_3-C_{18})$-heteroaryl, $(C_3-C_8)$-cycloalkyl, $(C_3-C_8)$-cycloalkenyl, H, $(C_1-C_8)$-alkyl, or $(C_2-C_8)$-alkenyl;

in a non-reactive organic solvent or solvent mixture with a bicyclic olefin of the formula (II):

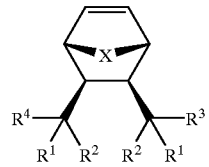

(II)

wherein:
- X is O, NR$^1$, C(R$^1$)$_2$, S, POR$^6$, or PR$^6$;
- R$^1$, R$^2$ are independently of each other H, $(C_1-C_8)$-alkyl, $(C_2-C_8)$-alkenyl, $(C_2-C_8)$-alkynyl, $(C_6-C_{18})$-aryl, $(C_7-C_{19})$-aralkyl, $(C_3-C_{18})$-heteroaryl, $(C_4-C_{19})$-heteroaralkyl, $(C_3-C_8)$-cycloalkyl, $(C_3-C_8)$-cycloalkenyl, $(C_6-C_{18})$-aryl-$(C_1-C_8)$-alkyl, $(C_3-C_{18})$-heteroaryl-$(C_1-C_8)$-alkyl, $(C_3-C_8)$-cycloalkyl-$(C_1-C_8)$-alkyl, or $(C_1-C_8)$-alkyl-$(C_3-C_8)$-cycloalkyl, or form together an =O group;
- R$^3$ and R$^4$ independently of each other, are OR$^1$, SR$^1$, NR$_2^1$, OR$^7$, SR$^7$ or NR$^5$R$^7$ provided that at least one residue R$^3$ or R$^4$ bears a group R$^7$;
- R$^6$ is R$^1$, provided that R$^6$ is not H; and
- R$^7$ is a catalytically active group;

and optionally with a further olefinic compound (III).

7. The method of claim 6, wherein in the respective formulae (I) and (II):

R is Ph;

X is O;

$R^1$ and $R^2$ form together an =O group;

$R^3$ is $R^4$, or $O(C_1-C_8)$-alkyl;

$R^4$ is $OR^7$.

8. The method of claim 7, wherein $R^7$ is a group comprising Taddol-ligands, chiral salene-complexes, ligands for Sharpless-dihydroxylation, 1,2-diaminoalcoholic groups or hydrogenation catalyst groups having 1,2-diphosphane ligands.

9. The method of claim 6, wherein the non-reactive organic solvent or part of the solvent mixture is a haloalkane.

10. The method of claim 6, wherein the process is conducted at a temperature of from −20° C. to 50° C.

11. The method of claim 7, wherein the ligands for Sharpless-epoxidation are dihydrochinidines.

12. The method of claim 8, wherein the ligands for Sharpless-epoxidation are dihydrochinidines.

* * * * *